United States Patent [19]

Casellas et al.

[11] Patent Number: 4,919,927
[45] Date of Patent: * Apr. 24, 1990

[54] PROCESS FOR THE POTENTIATION OF IMMUNOTOXINS

[75] Inventors: Pierre Casellas; Pierre Gros, both of Montpellier; Franz Jansen, St Mathieu de Treviers, all of France

[73] Assignee: Sanofi, Paris, France

[*] Notice: The portion of the term of this patent subsequent to Feb. 17, 2004 has been disclaimed.

[21] Appl. No.: 239,071

[22] Filed: Aug. 31, 1988

Related U.S. Application Data

[63] Continuation-in-part of Ser. No. 438,037, Nov. 1, 1982, Pat. No. 4,643,895.

[30] Foreign Application Priority Data

Nov. 20, 1981 [FR] France ................. 81 21836

[51] Int. Cl.$^5$ .................................. A61K 39/395
[52] U.S. Cl. ..................... 424/85.91; 530/387; 530/389; 530/391; 424/88; 514/885
[58] Field of Search ................. 530/387, 389–391; 424/85, 91, 88; 514/885

[56] References Cited

U.S. PATENT DOCUMENTS

| 4,485,093 | 11/1984 | Runge ................. 530/391 |
| 4,582,703 | 4/1986 | Jansen et al. ........... 424/85 |
| 4,614,650 | 9/1986 | Jansen et al. ........... 424/85 |
| 4,767,621 | 8/1988 | Jansen et al. ........ 424/85.91 |

OTHER PUBLICATIONS

Poncelet et al., "Present Potential of Immunotoxins", (Biosis Abstract) 1984, Behring Inst Mitt, 74, pp. 94–100.
Casellas et al., CA, vol. 104, 1986, #161626q.
Casellas et al., Int. J. Cancer, 30(4), 1982, pp. 437–443 (Abstract only).

Primary Examiner—Garnette D. Draper
Attorney, Agent, or Firm—Walter H. Schneider

[57] ABSTRACT

The present invention relates to a process for potentiating the activity of a conjugate consisting of the A chain of ricin coupled with an antibody directed against human T cells, the said process consisting in adding an effective quality of ammonium chloride to the said conjugate.

1 Claim, 8 Drawing Sheets

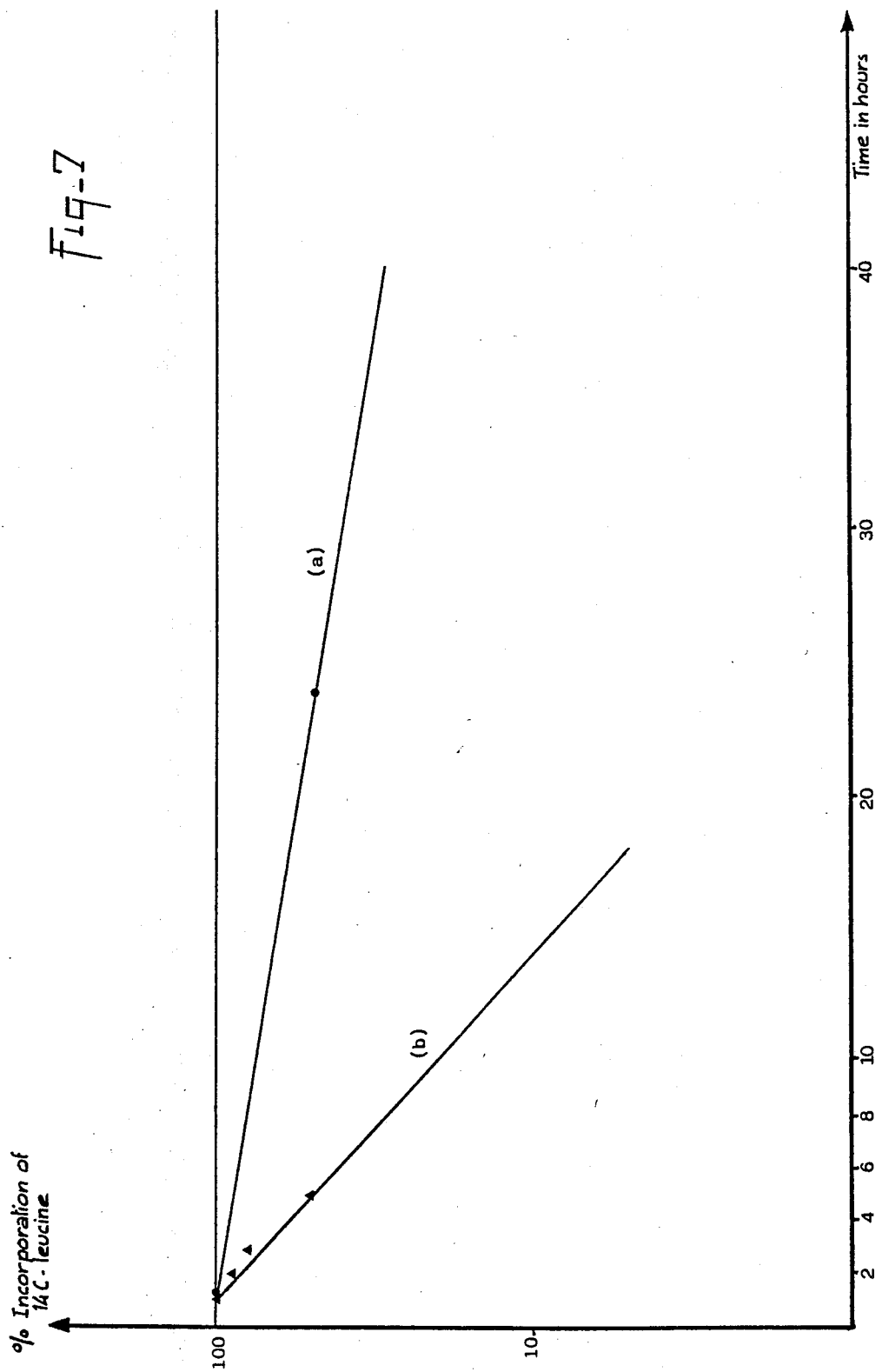

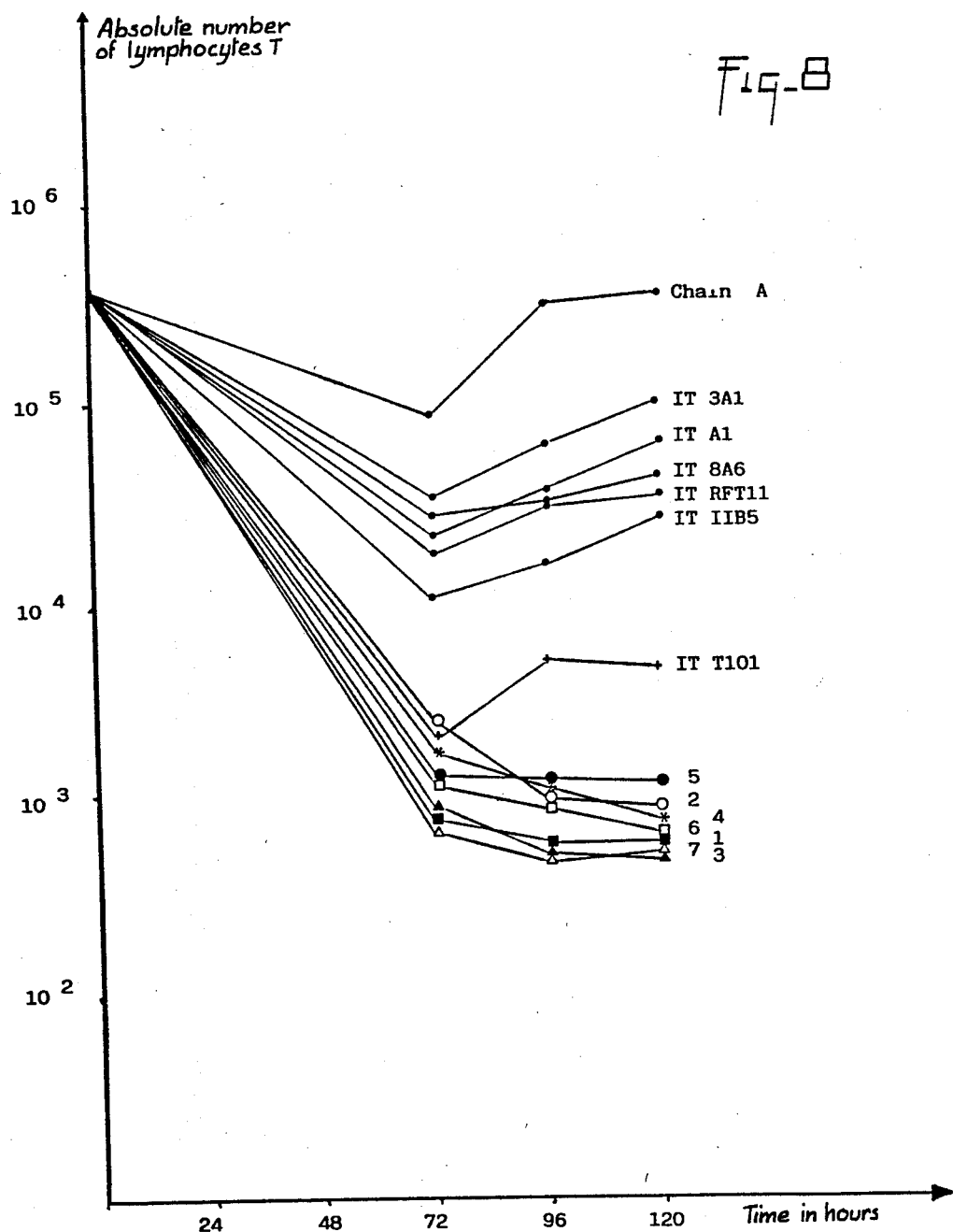

PROCESS FOR THE POTENTIATION OF IMMUNOTOXINS

The present patent application is a continuation-in-part application of U.S. Application 438037 filed on 1st Nov. 1982now U.S. Pat. No. 4,643,895.

In U.S. Pat. No. 4 340 535, there is described the preparation of anticancer products, called conjugates, obtained by coupling the A chain of ricin, by means of a covalent bond, with a protein structure, such as an antibody, an immunoglobulin or an immunoglobulin fragment, capable of selectively recognizing a given antigen on the surface of the target carrier cells, such as cancer cells. The principal property of these conjugates, which are also called immunotoxins, is that they are specific cytotoxic agents for the intended target cells.

The use of antibodies directed against cancer cell differentiation antigens had already made it possible to obtain conjugates exhibiting a considerable specificity towards the target cells.

The present invention relates to a process for potentiating the activity of these conjugates, which consists in adding an effective quantity of ammonium chloride to the said conjugates.

Conjugates are understood to mean artificial mixed molecules in which the A chain of ricin is associated, by a covalent bond of the disulfide type, with an antibody or an antibody fragment directed against human T cells, capable of selectively recognizing an antigen associated with target cells.

The preparation of the pure A chain of ricin has been described in our earlier patents. The preparation of monoclonal antibodies directed against human T leukemia cells has been mentioned in the scientific literature. (Reference may be made in particular to Journal of Immunology 125 (2), 725–731, (1980).)

To prepare the conjugates, the proteins to be coupled must each carry at least one sulfur atom which is naturally capable or has been artificially rendered capable of creating the desired disulfide bond.

The A chain of ricin naturally contains a single sulfur atom which permits the desired coupling. It belongs to the thiol group of the cysteine residue included in the A chain, which linked this A chain to the B chain in the complete toxin.

The whole antibody whose specificity is directed against human T cells contains neither a free thiol group nor other sulfur atoms capable of being used for coupling. If this whole antibody is used, one or more sulfur atoms capable of being subsequently incorporated into the disulfide bond to be formed with one or more molecules of A chain of ricin will therefore have to be introduced artificially into the immunoglobulin molecule.

If, on the other hand, the fragment Fab' of this antibody is used, as conventionally obtained by restricted proteolysis in the presence of pepsin and then reduction of the disulfide bridge (or bridges) between high-molecular chains, this fragment then possesses at least one thiol group available for creating the disulfide bridge with the A chain of ricin. In this latter case, according to the invention, the thiol group available on the antibody fragment will generally be converted to activated mixed disulfide by known methods before being reacted with the thiol of the A chain to create the desired disulfide group.

According to the invention, if the whole antibody is used, the conjugate is prepared by bringing the A chain of ricin, carrying its free SH group, into contact with the antibody into which the SH group has been artificially introduced in the activated form and especially in the form of a mixed disulfide with a suitable organic sulfur-containing radical.

The preparation of the conjugate can thus be represented by the equation:

RA-SH+AC-R-S-S-X→RA-S-S-R-AC+XSH in which:

RA denotes the A chain of ricin
AC denotes the antibody
X denotes the activating radical.

The antibody substituted by an activated sulfur atom is obtained from the antibody itself by substitution with a reagent (itself carrying an activated sulfur atom) according to the equation:

A+Y-R-S-S-X→AC-R-S-S-X in which:

AC denotes the antibody
Y represents a group permitting the covalent attachment of the reagent to the protein
R denotes a group capable of carrying the substituents Y and -S-S-X simultaneously
X denotes the activating radical.

The functional group Y is a group capable of bonding covalently with any one of the groups carried by the side chains of the constituent amino acids of the protein to be substituted. Of these groups, the terminal amino groups of the lysyl radicals contained in the protein are especially indicated. In this case, Y may represent in particular:

a carboxyl group which may bond to the amino groups of the protein in the presence of a coupling agent such as a carbodiimide and especially a water-soluble derivative such as 1-ethyl-3-(3-diethylamino-propyl)-carbodiimide, a carboxylic acid chloride which is capable of reacting directly with the amino groups to acylate them, a so-called "activated" ester, such as an ortho- or para-nitrophenyl or -dinitrophenyl ester or an N-hydroxysuccinimide ester, which reacts directly with the amine groups to acylate them, an internal anhydride of a dicarboxylic acid, for example succinic anhydride, which reacts spontaneously with the amine groups to create amide bonds, or an imidoester group:

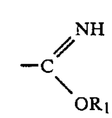

in which $R_1$ is an alkyl group reacting with the amine groups of the protein according to the equation:

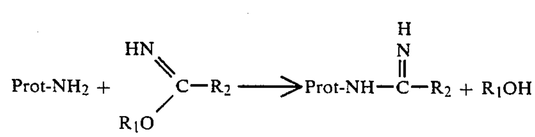

The radical -S-S-X denotes an activated mixed disulfide capable of reacting with a free thiol radical. In particular, in this mixed disulfide, X may denote a pyridin-2-yl or pyridin-4-yl group optionally substituted by one or more alkyl, halogen or carboxyl radicals. X can also denote a phenyl group preferably substituted by one or more nitro or carboxyl groups. X can also represent an alkoxycarbonyl group such as the methoxycarbonyl group.

The radical R denotes any radical capable of carrying the substituents Y and S-S-X simultaneously. It must be chosen so as not to contain groups which are liable to interfere, during the subsequent reactions, with the reagents used and the products synthesized. In particular, the group R can be a group —$(CH_2)_n$—, where n is between 1 and 10, or a group:

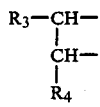

in which $R_4$ denotes hydrogen or an alkyl group having from 1 to 8 carbon atoms and $R_3$ denotes a substituent which is inert towards the reagents subsequently used, such as a carbamate group:

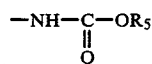

in which $R_5$ denotes a linear or branched alkyl group having from 1 to 5 carbon atoms, especially the tert.-butyl group.

The reaction of the compound Y-R-S-S-X with the immunoglobulin is carried out in the homogeneous liquid phase, most frequently in water or a buffer solution. If the solubility of the reagents requires it, it is possible for up to 20% by volume of a water-miscible organic solvent, such as an alcohol, especially tertiary butanol, to be added to the reaction medium.

The reaction is carried out at room temperature for a period varying from a few hours to 24 hours. After this, the low-molecular products and in particular the excess reagents can be removed by dialysis. This process makes it possible to introduce between 1 and 5 substituent groups per mol of protein if the protein is a class G immunoglobulin or between 1 and 15 if the protein is a class M immunoglobulin.

When using such compounds, the coupling with the A chain of ricin is carried out by bringing the two proteins into contact in aqueous solution at a temperature not exceeding 30° C. and for a period varying from a few hours to one day. The solution obtained is dialyzed to remove the low-molecular products and the conjugate can then be purified by a variety of known methods.

By themselves, the conjugates prepared by the above process have a strong specific cytotoxic activity towards human T cell lines. They can therefore be used in human therapy to treat T leukemia or any other cancerous or non-cancerous complaint calling for the selective destruction of cells which would be sensitive to the conjugate prepared according to the invention. This can be envisaged in transplantations or in certain autoimmune diseases for reducing the activity of the T lymphocytes or this type of subpopulation of T lymphocytes.

Ammonium chloride has a very substantial potentiating effect on the activity of these conjugates towards the corresponding target cells. It has in fact been observed that the presence of $NH_4Cl$ considerably accelerates the kinetics of expression of the cytotoxicity of these conjugates.

This kind of accelerating effect is of the greatest importance for all therapeutic applications because the speed of action of the drug is always a favorable factor in the efficacy of the treatment.

It is possible to utilize this new property to enhance the therapeutic efficacy of the conjugate in the treatment of the diseases to which it is applied. This improvement can be exploited according to two different therapeutic schemes:

(a) Samples of human bone marrow, taken especially from leukemia patients, can be treated in vitro with the conjugate in the presence of ammonium chloride. As this association has a very high and very specific cytotoxic efficacy, any cell carrying the antigen recognized by the conjugate, in particular any tumoral cell, can be removed from the marrow treated in this way. Furthermore, the patient can be treated by any appropriate therapy, such as radiotherapy and/or chemotherapy, at a supralethal dose, so as to remove the tumoral cells from his organism. Finally, the marrow purified in the manner indicated is transplanted back into the patient's organism in the form of an autologous graft to allow the reconstitution of the populations of blood cells destroyed by the supralethal treatment.

(b) The application of the potentiating property of ammonium chloride to the patient in vivo can also be exploited to obtain the maximum efficacy of the conjugate. In fact, it has been shown that mice into which tumoral cells have previously been transplanted, and to which the conjugate is administered at the same time as 3 injections of 7 mg of ammonium chloride at 15-minute intervals, exhibit a better percentage survival rate and a better inhibition of tumor growth than control mice which have only received the conjugate.

These conjugates are packaged for administration by injection. They can be used by themselves, or associated with ammonium chloride, or associated with another treatment for the cancerous complaint in question and, in particular, associated with other immunodepressant drugs so as to delay and weaken the natural immune reaction of the patient towards the protein foreign to his organism, which the conjugate represents.

With the aim of eliminating all the cancer cells, the treatment must be carried out with a sufficient dose of conjugate and the duration of the treatment must be determined in each case according to the subject and the nature of the complaint to be treated.

The examples which follow provide a clearer understanding of the invention without limiting its scope.

The A chain of ricin used in each of the examples below was prepared and purified by the process described in French Pat. Nos. 78 27838 and 79 24655, to which U.S. Pat. No. 4 340 535 corresponds.

Moreover, a study performed by cytofluorometry made it possible to show that the anti-human T cell antibody used, the corresponding activated antibody and the conjugate of this antibody with the A chain of ricin had superimposable fluorescence histograms, allowing the assertion that the antibody had not undergone any significant degradation during the activation and coupling reactions to which it had been subjected and, in particular, that it was still capable, even within the conjugate, of recognizing the human T antigen against which it was directed.

Furthermore, each conjugate obtained was studied for its biological properties and, more especially, its anticancer action.

BRIEF DESCRIPTION OF THE DRAWINGS

FIG. 7 shows the acceleration of cytotoxicity kinetics of the immunotoxins anti-T carried out on cells of the P12/ICHIKAWA line when potentiated with ammonium chloride.

FIG. 8 shows the effect on the proliferation of human T lymphocytes stimulated in the presence of various immunotoxins and ammonium chloride, and in the presence of various associations of immunotoxins and ammonium chloride.

Figure 1:
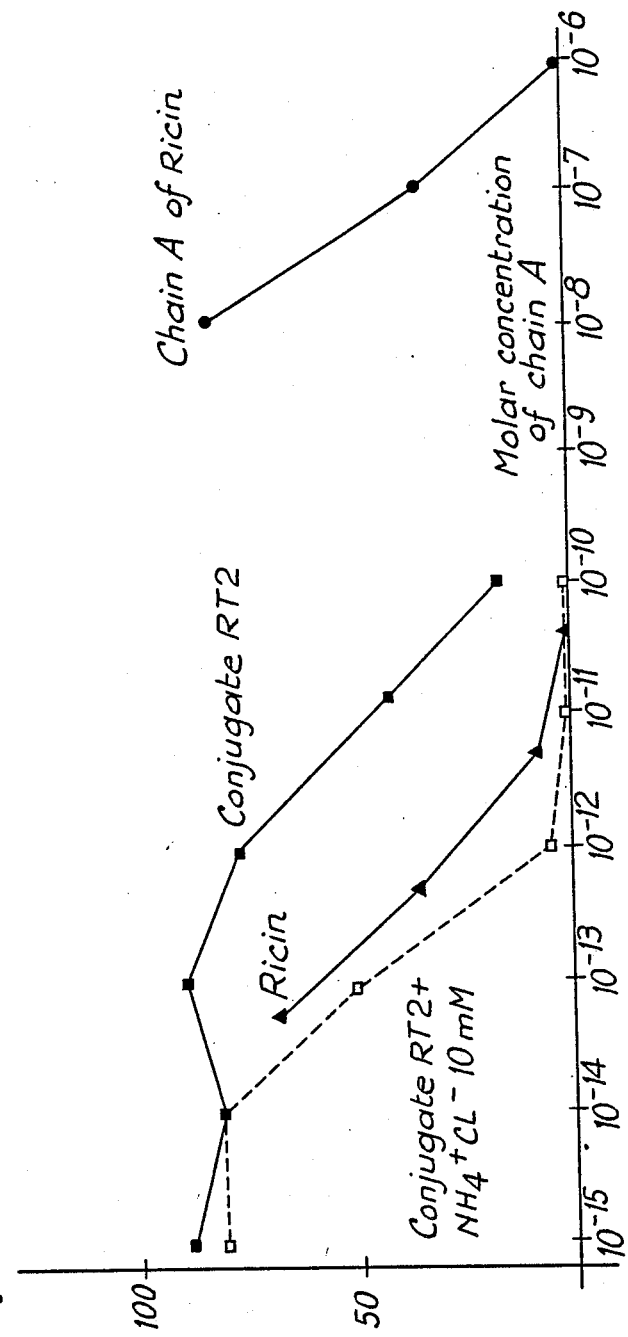
FIG. 1 shows the cytotoxic activity on cells of the CEM cell line derived from a human T leukemia which carries the antigen T65, obtained with ricin, the A chain of ricin and the conjugate RT2(a compound prepared according to this invention) in the presence and absence of ammonium chloride.
Figure 2:
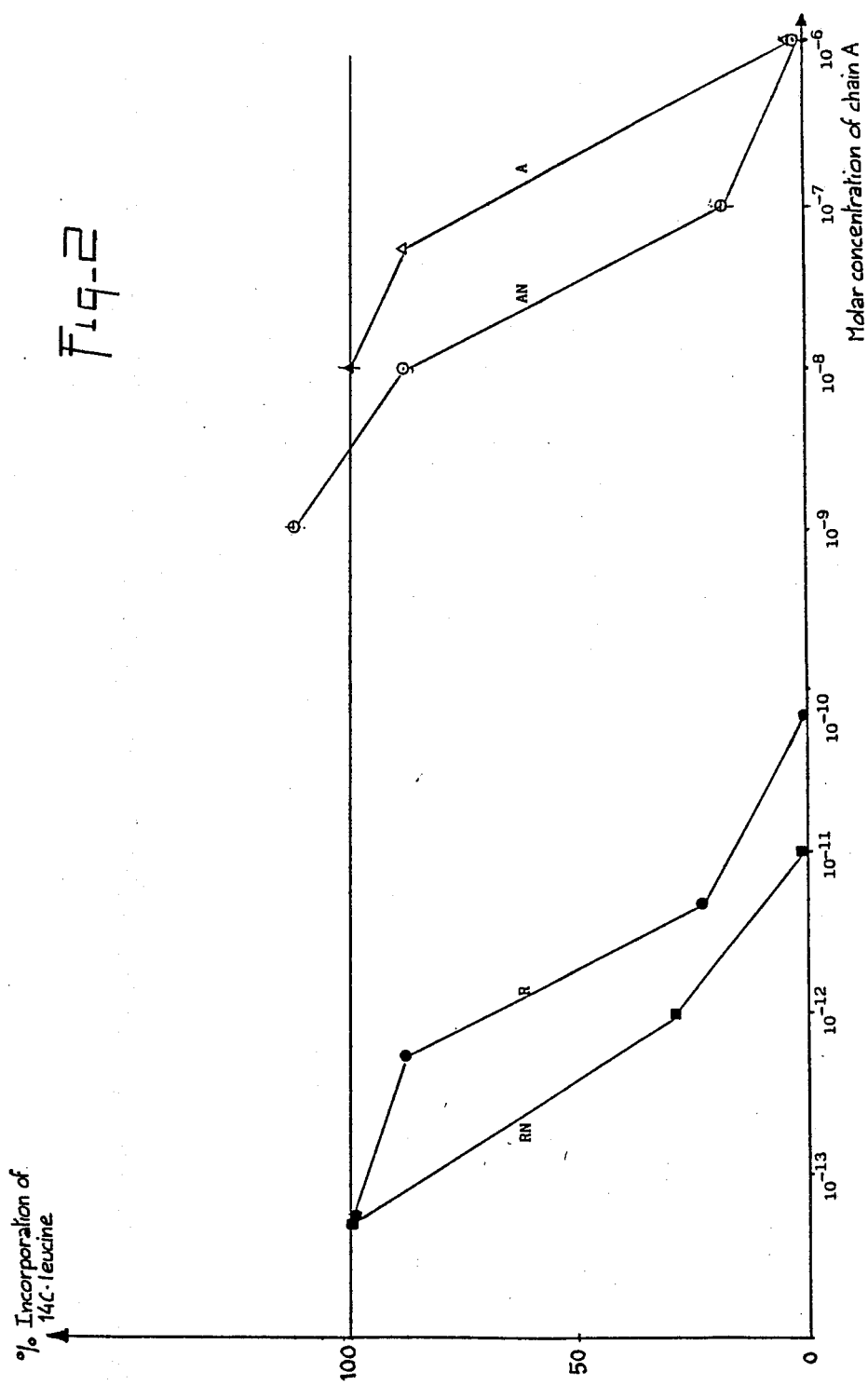
FIG. 2 shows the cytotoxic activity on human T lymphoblastoid cells of the CEM line obtained with ricin and the A chain of ricin in the presence and absence of ammonium chloride.
Figure 3:
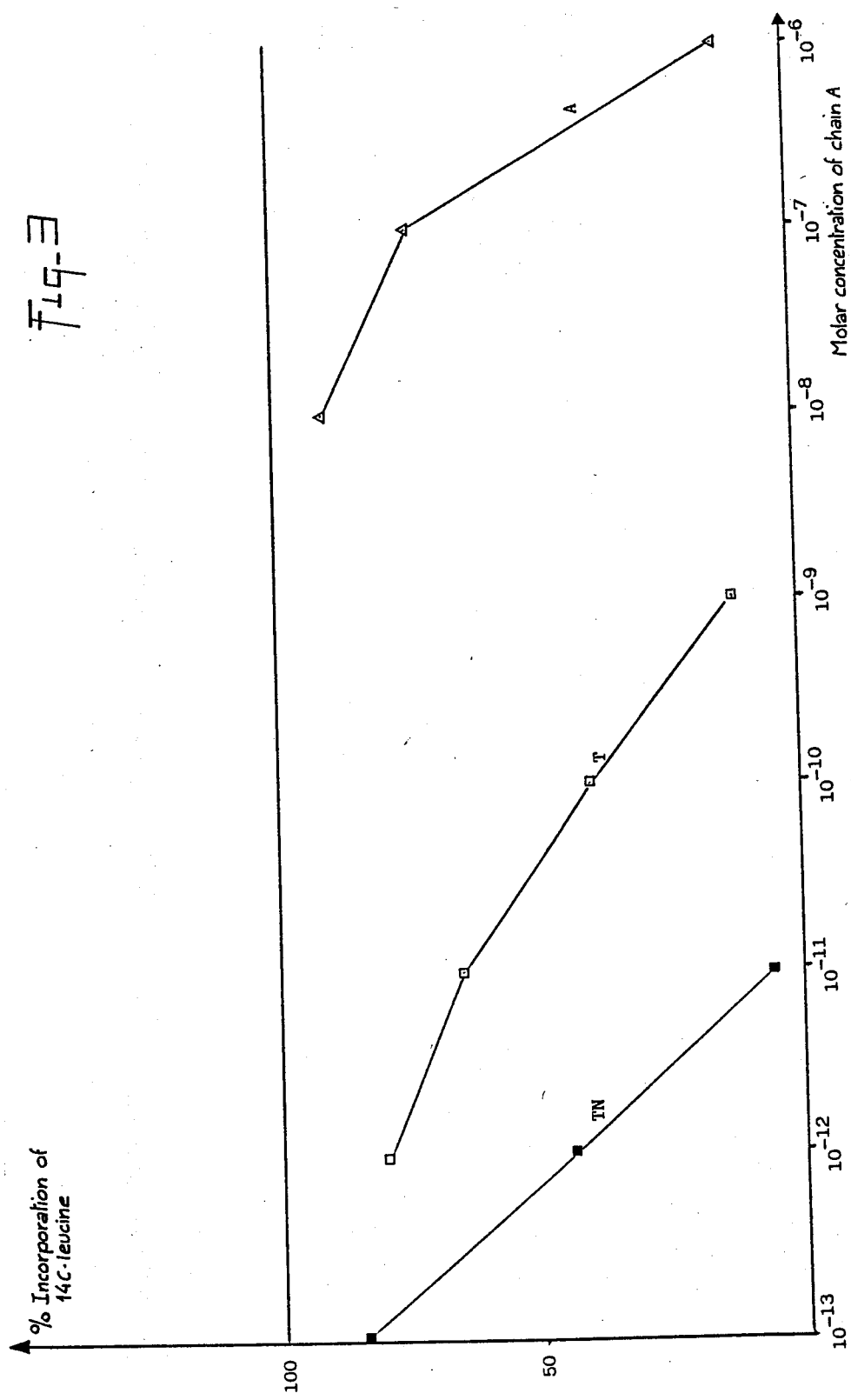
FIG. 3 shows cytotoxic activity on the same CEM cells obtained with the A chain of ricin, immunotoxin anti-T and immunotoxin anti-T+ammonium chloride.

EXAMPLE 1:

Conjugate obtained by reacting an antihuman T cell antibody (antibody directed against the antigen T65), substituted by an activated disulfide group, with the A chain of ricin (a) Anti-human T cell antibody (or antibody T101)

This antibody was obtained by the method described in Journal of Immunology 125 (2), 725–731, (1980).

It undergoes a final purification by dialysis against PBS buffer (10 mM of phosphate, 140 mM of sodium chloride, pH 7.4).

(b) Activated anti-human T cell antibody 0.1 ml of a solution containing 42.7 mg/ml of 1-ethyl-3-(3-dimethylaminopropyl)carbodiimide is added to 0.5 ml of a solution containing 14.2 mg/ml of 3-(pyridin-2-yldisulfanyl)propionic acid in tert.-butanol and the mixture is left at room temperature for 3 minutes.

180 μl of the resulting solution are added to 5.6 ml of an antibody solution containing 3.6 mg/ml in PBS buffer. Incubation is allowed to proceed for 20 hours at 30° C.

The solution is then dialyzed continuously for 3 days against 21 liters of PBS buffer at 4° C. This gives 16 mg of activated antibody at a concentration of 2.6 mg/ml.

By spectrophotometric analysis at 343 nm of the pyridine-2-thione released by exchange with reduced glutathion, it is found that the antibody obtained carries 3.1 activating groups per mol of antibody.

(c) Conjugate 0.87 ml of a solution of A chain of ricin in PBS buffer (concentration 6.6 mg/ml) is added to 4.6 ml of a solution of activated antibody in the same buffer (concentration 2.6 mg/ml, i.e. 12 mg of activated antibody) and incubation is carried out for 20 hours at 25° C.

The reaction mixture is chromatographed on a column of Sephadex G100 gel. In each fraction, the antibody concentration is determined by spectrophotometry at 280 nm and the A chain concentration is determined by its power to inhibit protein synthesis measured on an acellular system. The identical fractions containing the conjugate are combined to give about 11 mg of the conjugate at a concentration of 0.8 mg/ml.

The analytical determinations performed make it possible to show that the solution contains 140 μg/ml of biologically active A chain, i.e. about 1.1 mol of A chain per mol of antibody.

(1) INHIBITION OF PROTEIN SYNTHESIS

The fundamental biological property of the A chain of ricin is to inhibit protein synthesis in cells by degradation of the ribosomal subunit 60S.

A cellular model was used here. This test measures the effect of the substances studied on the incorporation of $^{14}C$-leucine into cancer cells in culture.

The cells used belong to the CEM cell line derived from a human T leukemia which carries the antigen T65. The cells are incubated in the presence of the substance to be studied, and then, when incubation has ended, the degree of incorporation of $^{14}C$-leucine by the cells treated in this way is measured.

This measurement is made by a technique adapted from the one described in Journal of Biological Chemistry 1974, 249 (11), 3557-62, using the tracer $^{14}C$-leucine to determine the degree of protein synthesis. The radioactivity incorporated is determined here on the whole cells isolated by filtration.

On the basis of these determinations, it is possible to draw the dose/effect curves, plotting, on the abscissa, the molar concentration of A chain in the substances studied, and, on the ordinate, the incorporation of $^{14}C$-leucine expressed as a percentage of the incorporation by control cells in the absence of any substance affecting protein synthesis.

It is thus possible to determine, for each substance studied, the concentration which causes a 50% inhibition of incorporation of $^{14}C$-leucine, or "50% inhibitory concentration" ($IC_{50}$).

FIG. 1 shows the curves obtained in the same experiment with ricin, with its free A chain and with the conjugate RT2 (a compound prepared according to Example 1), in the presence and absence of 10 mM ammonium chloride in the incubation medium. Even in the absence of ammonium chloride and after incubation for 48 h, it can be seen on this figure that the conjugate studied, RT2, has a strong cytotoxic activity ($IC_{50} = 7 \times 10^{-12}$ M) which is about 7000 times greater than that of the A chain of ricin.

(2) - POTENTIATION OF THE ACTIVITY OF THE CONJUGATE RT2 BY AMMONIUM CHLORIDE

FIG. 1 also shows that the presence of 10 mM ammonium chloride in the medium for incubating the cells with the conjugate RT2 very greatly increases—by a factor of about 80—the cytotoxic activity of the conjugate on the target cells. This potentiating effect is not obtained with ricin, with the A chain or with a conjugate which is non-specific for the cells studied. Thus, in the presence of ammonium chloride as a potentiator, the cytotoxic activity of the conjugate ($IC_{50} = 8.5 \times 10^{-14}$ M) becomes about 600,000 times higher than that of the A chain by itself and even potentially exceeds the activity of ricin, which has never been described for any conjugate between the A chain of ricin and any type of antibody.

EXAMPLE 2:

Conjugate obtained by reacting an anti-human T cell antibody (antibody directed against an antigen of MW=40 KD), substituted by an activated disulfide group, with the A chain of ricin A - Anti-human T cell antibody (or antibody T3-A1)

This antibody, deposited at the ATCC under the number HB2, is an IgG1; it is directed against CD7 (in: Leucocyte typing, A. Bernard, L. Boumssell, C. Milstein J. Dausset and S. F. Schlossman editors, Springer Verlag, Berlin, 1984, ref. 1).

This antibody was obtained by the method described in Proc. Natl. Acad. Sci. U.S.A., 1979, 76, 5829. It undergoes a final purification by dialysis against phosphate buffer (125 mM, pH 7.0).

B - Activated anti-human T cell antibody 94 mg of antibody T3-A1 are modified with 7.6 mg of pyridyldithiopropionic acid, activated beforehand by reaction with 4.4 mg of ethyldimethylaminopropylcarbodiimide, in a total volume of 13 ml of phosphate buffer (125 mM, pH 7.0) for 15 min at room temperature. The IgGs modified in this way are purified by dialysis against the same phosphate buffer (125 mM, pH 7.0) to remove the excess reagents.

C - Conjugate (immunotoxin)

82.5 mg of modified antibodies are incubated for 20 h at 25° C. with 28.4 mg of A chain of ricin. The reaction medium is then purified y chromatography on Sephadex G100. The immunotoxin is obtained in the first chromatography peak.

D - Biological properties (1) Inhibition of protein synthesis in cells and potentiation of this effect The cytotoxicity is evaluated by measuring the incorporation of $^{14}C$-leucine by the cells after incubation for 18 h at 37° C. in the presence of known quantities of the immunotoxin studied, or reference cytotoxic substances, in the presence or absence of ammonium chloride as a potentiator.

The results of the experiments performed are presented in the form of dose/effect curves, plotting, on the ordinate, the cytotoxic effect evaluated as indicated above and calculated in % of the value obtained on control cells in the absence of any cytotoxic substance, and, on the abscissa, the concentrations of the cytotoxic substances studied, expressed as molar concentrations of the toxic subunits of these substances (molar concentration of A chain of ricin).

Ammonium chloride was tested at a concentration of 10 mM. A previous check had been carried out to ensure that $NH_4Cl$ is not spontaneously cytotoxic to the cells employed at the concentrations indicated.

FIG. 2 shows the respective results obtained on human T lymphoblastoid cells of the CEM line.

The experimental conditions used and the symbols employed to characterize the curves obtained are indicated in the table below:

| | |
|---|---|
| A chain of ricin | A |
| ricin | R |
| A chain + $NH_4Cl$ 10 mM | AN |
| ricin + $NH_4Cl$ 10 mM | RN |

FIG. 2 shows the effects of ammonium chloride on the inherent cytotoxicity of ricin and isolated A chain, taken as reference substances. The values of the molar concentrations corresponding to a 50% inhibition of incorporation of the tracer ($IC_{50}$) are indicated in Table I.

TABLE I

| Substances tested | on CEM cells With $NH_4Cl$ 10 mM | Without activator |
|---|---|---|
| Ricin | $3.8\cdot10^{-13}$ | $2\cdot10^{-12}$ |
| A chain | $3.8\cdot10^{-8}$ | $2.2\cdot10^{-7}$ |

FIG. 3 shows the respective results obtained on the same CEM cells for:

| | |
|---|---|
| A chain of ricin | A |
| immunotoxin anti-T | T |
| immunotoxin anti-T + $NH_4Cl$ 10 mM | TN |

The figure shows the comparative potentiating effect of the ion $NH_4^+$ (10 mM) on the cytotoxicity of the immunotoxin anti-T towards cells of the CEM line.

The values of the molar concentrations corresponding to a 50% inhibition of incorporation of the tracer ($IC_{50}$) are recorded in Table II.

TABLE II

| | | on CEM cells Molar concentrations corresponding to 50% inhibition of incorporation of the tracer | |
|---|---|---|---|
| Example | Antibody | $IC_{50}$ of non-potentiated immunotoxin | $IC_{50}$ of immunotoxin potentiated by $NH_4Cl$ 10 mM |
| 2 | T3-A1 | $5\cdot10^{-11}$ | $7\cdot10^{-13}$ |
| 3 | LAU A1 | $6\cdot10^{-10}$ | $2\cdot10^{-11}$ |
| 4 | RFT2 | $4\cdot10^{-11}$ | $5\cdot10^{-12}$ |
| 5 | 8H8.1 | $3\cdot10^{-11}$ | $4\cdot10^{-12}$ |
| 6 | 8A6 | $3\cdot10^{-10}$ | $2\cdot10^{-11}$ |
| 7 | Fab 8A6 | $4\cdot10^{-10}$ | $7\cdot10^{-12}$ |
| 8 | 6D9 | $3\cdot10^{-10}$ | $2\cdot10^{-12}$ |
| 9 | Fab T101 | $3.5\cdot10^{-10}$ | $2.6\cdot10^{-12}$ |
| 10 | $F(ab')_2$ T101 | $5\cdot10^{-11}$ | $6\cdot10^{-13}$ |

The results obtained show that, in the CEM cell model, the potentiating effect of the ammonium ion is of the order of 71. This factor is considerably higher than those observed on ricin or isolated A chain. The result of this is that, in the presence of $NH_4Cl$, the specific cytotoxicity of the immunotoxin anti-T (3A1) towards its target, in the presence of $NH_4Cl$, is equivalent to that of ricin itself.

Moreover, the ammonium ion has the remarkable properties of not only potentiating the activity but also increasing the selectivity of the immunotoxin. In fact, if the ratio of the $IC_{50}$ values of the free A chain and the immunotoxin is taken as the criterion for selectivity of action of the immunotoxin, this ratio is 4,400 in the absence of activator and 54,000 in the presence of $NH_4Cl$.

(2) Acceleration of the cytotoxicity kinetics

The effect of ammonium chloride is not restricted to considerably increasing the cytotoxic activity of the immunotoxins; it also makes it possible very substantially to accelerate the kinetics of the immunotoxins, as demonstrated by the following experiment.

By way of example, this experiment measured, as previously, the incorporation of radioactive tracer into the cells incubated with the immunotoxin, in the absence or presence of $NH_4Cl$ 10 mM as a potentiator.

Figure 4:
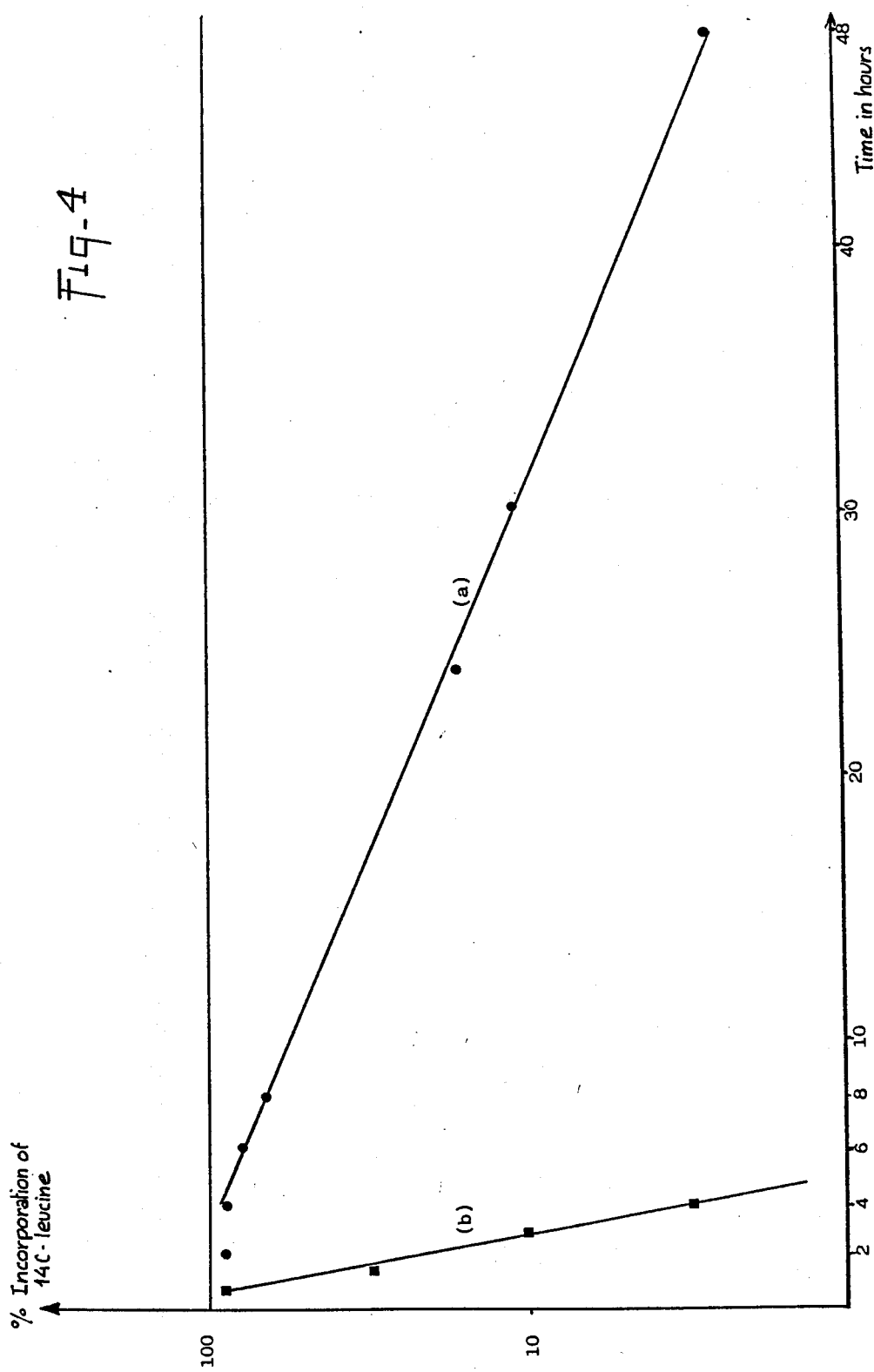
FIG. 4 shows the acceleration of cytotoxicity kinetics of the immunotoxin anti-T carried out on CEM cells when potentiated with ammonium chloride.

This experiment was carried out on the cellular model consisting of the CEM human T lymphoblastoid line with the immunotoxin anti-T at a concentration of $10^{-8}$ M. The results are presented in FIG. 4. This figure shows the results obtained by plotting the percentage incorporation of $^{14}C$-leucine (% of the control values) on the ordinate and the time in hours on the abscissa.

It is seen that, in the absence of potentiation, the expression of the cytotoxicity is very slow, as shown in curve (a). The value T10, which is the time required to obtain a 90% reduction in the incorporation of the tracer, is of the order of 30 h. On the other hand, in the presence of $NH_4Cl$ 10 mM, a considerable acceleration of the kinetics of expression of the cytotoxicity is apparent—curve (b)—since the value T10 is only 3 h here.

(3) Inhibition of the proliferation of stimulated human T lymphocytes

In physiological and pathological situations, as in numerous experimental models, the T lymphocytes isolated from peripheral blood or from bone marrow have the property of responding to a variety of stimulations by proliferating. It is this proliferative response which we studied.

By way of example, lymphocytes from human peripheral blood, purified by Ficoll gradient centrifugation, are incubated in the presence of known concentrations of immunotoxin or reference cytotoxic substance and a final concentration of 10 mM of ammonium chloride for 24 h at 37° C. The cells are then washed and brought into contact with a mitogenic agent specific for human T cells, which consists of a mixture of phytohemagglutinin A (PHA) (Wellcome Ltd., 1% final concentration) and "T cell growth factor" (or TCGF or interleukine 2 or IL2) at a final concentration of 0.5 unit/ml. The residual cells capable of proliferating are analyzed 72, 96 and 120 h after the cytotoxic treatment has ended by means of indirect immunofluorescence using a flux cytofluorometer (FACS IV Becton Dickinson).

The results are presented in FIG. 8 (curve IT 3A1).

EXAMPLE 3:

Conjugate obtained by reacting an anti-human T cell antibody (antibody directed against an antigen of MW = 40 KD), substituted by an activated disulfide group, with the A chain of ricin A - Anti-human T cell antibody (or antibody LAU A1)

This antibody, which is directed against CD7 (ref. 1), is an IgG2. It was obtained by the method described in Molecular Immunology 21 (10), 831–840, 1984. It undergoes a final purification by dialysis against phosphate buffer (125 mM, pH 7.0).

B - Activated anti-human T cell antibody 32.5 mg of antibody LAU A1 are modified with 2.1 mg of pyridyldithiopropionic acid, activated beforehand with 1.25 mg of ethyldimethylaminopropylcarbodiimide, in a total volume of 5 ml of phosphate buffer (0.125 M, pH 7.0) for 15 min at room temperature. The IgGs modified in this way are purified by dialysis against the same phosphate buffer (125 mM, pH 7.0) to remove the excess reagents.

C - Conjugate (immunotoxin)

27.6 mg of modified antibodies are incubated for 5 h at 25° C. with 11.0 mg of A chain of ricin. The reaction medium is then purified by chromatography on Sephadex G100. The immunotoxin is obtained in the first chromatography peak.

Moreover, a study performed by cytofluorometry made it possible to show that the anti-human T cell antibody used, the corresponding activated antibody and the conjugate of this antibody with the A chain of ricin had superimposable fluorescence histograms, allowing the assertion that the antibody had not undergone any significant degradation during the activation and coupling reactions to which it had been subjected and, in particular, that it was still capable, even within the conjugate, of recognizing the human T antigen against which it was directed.

The conjugate according to the invention, obtained above, was studied for its biological properties and, more especially, its anticancer action.

D - Biological properties (1) Inhibition of protein synthesis in cells and potentiation of this effect The study is performed according to D(1) of Example 2 of the present patent application.

The values of the molar concentrations corresponding to a 50% inhibition of incorporation of the tracer ($IC_{50}$) are indicated in Table II.

They show that the potentiating effect of the ammonium ion is 30 and that it is greater than that of the same ion on isolated A chain.

(2) Acceleration of the cytotoxicity kinetics

Following the procedure described in Example 2, it is seen that, in the absence of potentiation, the expression of the cytotoxicity is very slow. The value T10, which is the time required to obtain a 90% reduction in the incorporation of the tracer, is of the order of 20 h. On the other hand, in the presence of $NH_4Cl$ 10 mM, a considerable acceleration of the kinetics of expression of the cytotoxicity is apparent since the value T10 is only 2 h here.

(3) Inhibition of the proliferation of stimulated human T lymphocytes

The studies are performed according to D(3) of Example 2 of the present patent and the results are expressed in FIG. 8 (curve IT A1).

EXAMPLE 4:

Conjugate obtained by reacting an anti-human T cell antibody (antibody directed against an antigen of MW = 40 KD), substituted by an activated disulfide group, with the A chain of ricin A - Anti-human T cell antibody (or antibody RFT2)

This antibody, which is directed against CD7 (ref. 1), is an IgG2a. It was obtained by the method described in Leucocyte typing: A. Bernard, L. Boumssell, J. Dausset, C. Milstein, S. F. Schlossman editors, Springer Verlag, 1984, 469–475 Ref. 3. It undergoes a final purification by dialysis against phosphate buffer (125 mM, pH 7.0).

B - Activated anti-human T cell antibody 10 mg of antibody RFT2 are modified with 0.65 mg of pyridyldithiopropionic acid, activated beforehand with 0.38 mg of ethyldimethylaminopropylcarbodiimide, in a total volume of 3.5 ml of phosphate buffer (0.125 M, pH 7.0) for 15 min at room temperature. The IgGs modified in this way are purified by dialysis against the same phosphate buffer (125 mM, pH 7.0) to remove the excess reagents.

C - Conjugate (immunotoxin)

6.8 mg of modified antibodies are incubated for 17 h at 25° C. with 3.4 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect The study is performed according to D(1) of Example 2 of the present patent application.

The values of the molar concentrations corresponding to a 50% inhibition of incorporation of the tracer ($IC_{50}$) are indicated in Table II. These values show that the potentiating effect of the ammonium ion is 10. Moreover, it increases especially the selectivity of the immunotoxin. In fact, if the ratio of the $IC_{50}$ values of the isolated A chain and the immunotoxin is taken as the criterion for selectivity of action of the immunotoxin, this ratio is 5,500 in the absence of activator and 7,600 in the presence of $NH_4Cl$.

(2) Acceleration of the cytotoxicity kinetics

Following the procedure described in Example 2, section D(2), the expression of the cytotoxicity is seen to be very slow in the absence of potentiation. The value T10, which is the time required to obtain a 90% reduction in the incorporation of the tracer, is more than 100 h. On the other hand, in the presence of $NH_4Cl$ 10 mM, a considerable acceleration of the kinetics of expression of the cytotoxicity is apparent since the value T10 is only 4 h here.

EXAMPLE 5:

Conjugate obtained by reacting an anti-human T cell antibody (antibody directed against an antigen of MW=40 KD), substituted by an activated disulfide group, with the A chain of ricin A - Anti-human T cell antibody (or antibody 8H8.1)

This antibody, which is directed against CD7 (ref. 1), is an IgG2a. It was obtained by the method described by C. Mawas, Marseille Luminy, France. It undergoes a final purification by dialysis against phosphate buffer (125 mM, pH 7.0).

B - Activated anti-human T cell antibody 20 mg of antibody 8H8.1 are modified with 1.3 mg of pyridyldithiopropionic acid, activated beforehand by reaction with 0.77 mg of ethyldimethylaminopropylcarbodiimide, in a total volume of 8.7 ml of phosphate buffer (0.125 M, pH 7.0) for 15 min at room temperature. The IgGs modified in this way are purified by dialysis against the same phosphate buffer (125 mM, pH 7.0) to remove the excess reagents.

C - Conjugate (immunotoxin)

18.2 mg of modified antibodies are incubated for 5 h at 25° C. with 8.2 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect The study is performed according to D(1) of Example 2 of the present patent application.

The values of the molar concentrations corresponding to a 50% inhibition of incorporation of the tracer ($IC_{50}$) are indicated in Table II.

(2) Acceleration of the cytotoxicity kinetics

Following the procedure of Example 2, section D(2), of the application, it is seen that, in the absence of potentiation, the expression of the cytotoxicity is very slow. The value T10, which is the time required to obtain a 90% reduction in the incorporation of the tracer, is of the order of 16 h. On the other hand, in the presence of $NH_4Cl$ 10 mM, a considerable acceleration of the kinetics of expression of the cytotoxicity is apparent since the value T150 is only 3 h 30 min here.

EXAMPLE 6:

Conjugate obtained by reacting an anti-human T cell antibody (antibody directed against an antigen of MW=40 KD), substituted by an activated disulfide group, with the A chain of ricin A - Anti-human T cell antibody (or antibody 8A6)

This antibody, which is directed against CD7 (ref. 1), is an IgG1. It was obtained by D. Carriere, Centre de Recherche Clin-Midy/Sanofi, Montpellier, France, in the following manner: 4 weeks after the immunization of Balb/c mice with $10^7$ cells of the CEM human T lymphoblastoid line by intraperitoneal administration, a booster is administered intravenously with the same number of immunizing cells. Three days after the booster, the spleen cells of the immunized mice are fused with myeloma cells of the NS2 murine line in the presence of PEG 40%. The clone F938A6 was selected because of its specificity for human T cells. This purified antibody undergoes a final dialysis against phosphate buffer (125 mM, pH 7.0).

B - Activated anti-human T cell antibody 20 mg of antibody 8A6 are modified with 0.5 mg of pyridyldithiopropionic acid, activated beforehand with 0.3 mg of ethylmethylaminopropylcarbodiimide, in a total volume of 3.03 ml of phosphate buffer (0.125 M, pH 7.0) for 30 min at room temperature. The IgGs modified in this way are purified by dialysis against the same phosphate buffer (125 mM, pH 7.0) to remove the excess reagents.

C - Conjugate (immunotoxin)

6.47 mg of modified antibodies are incubated for 20 h at 25° C. with 5.52 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect The study is performed according to D(1) of Example 2 of the present application.

The values of the molar concentrations corresponding to a 50% inhibition of incorporation of the tracer ($IC_{50}$) are recorded in Table II. They show that the potentiating effect of the ammonium ion is 15 on the CEM cells.

(2) Inhibition of the proliferation of stimulated human T lymphocytes

The studies are performed according to D(3) of Example 2 of the present application.

The results are presented in FIG. 8 (curve IT 8A6).

EXAMPLE 7:

Conjugate obtained by reacting an anti-human T cell antibody fragment (antibody fragment directed against an antigen of MW=40 KD). substituted by an activated disulfide group, with the A chain of ricin

A - Anti-human T cell antibody fragment (or Fab 8A6)

The antibody fragment 8A6, or Fab 8A6, was obtained from the antibody 8A6 described in Example 6 above. 100 mg of antibody 8A6 are hydrolyzed with 1 mg of papain for 3 h at 37° C. in the presence of cysteine 10 mM and EDTA 1 mM. The reaction is stopped with iodoacetamide 20 mM for 1 h at 37° C. and the reaction medium is dialyzed against phosphate buffer (10 mM, pH 7.0). The reaction medium is chromatographed on DEAE trisacryl. The antibody fragments 8A6 are recovered in the filtrate.

B - Activated anti-human T cell antibody fragment 40 mg of Fab 8A6 are modified with 2.01 mg of SPDP (N-hydroxysuccinimide ester of pyridin-2-yldithiopropionic acid) in a total volume of 7.5 ml of phosphate buffer (0.125 M, pH 7.0) for 30 min at room temperature. The IgGs modified in this way are purified by dialysis against the same phosphate buffer (125 mM, pH 7.0) to remove the excess reagents.

C - Conjugate (immunotoxin)

29 mg of modified antibody fragments 8A6 are incubated for 17 h at 25° C. with 55 mg of A chain of ricin. The reaction medium is then purified by chromatography on Biogel P100. The immunotoxin is obtained in the first chromatography peak.

D - Biological properties (1) Inhibition of protein synthesis in cells and potentiation of this effect The study is performed according to D(1) of Example 2 of the present application.

The values of the molar concentrations corresponding to a 50% inhibition of incorporation of the tracer ($IC_{50}$) are recorded in Table II. These values show that the potentiating effect of the ammonium ion is 57. Moreover, it increases especially the selectivity of the immunotoxin. In fact, if the ratio of the $IC_{50}$ values of the isolated A chain and the immunotoxin is taken as the criterion for selectivity of action of the immunotoxin, this ratio is 550 in the absence of activation and 5,400 in the presence of $NH_4Cl$.

EXAMPLE 8:

Conjugate obtained by reacting an anti-human T cell antibody (antibody directed against an antigen of MW=65 KD), substituted by an activated disulfide group, with the A chain of ricin

A - Anti-human T cell antibody (or antibody 6D9)

This antibody, which is directed against CD5 (ref. 1), is an IgG2a. It was obtained by D. Carriée, Centre de Recherche Clin-Midy/Sanofi, as for Example 6 of the present patent application.

The clone F936D9 was selected because of its specificity for human T cells. This purified antibody underwent a final dialysis against a phosphate buffer (125 mM, pH 7.0).

B - Activated anti-human T cell antibody 31 mg of antibody 6D9 are modified with 0.033 mg of SPDP in a total volume of 1.270 ml of buffer (pH 9.0) for 15 min at room temperature. The IgGs modified in this way are purified by dialysis against the same buffer (pH 9.0) to remove the excess reagents.

C - Conjugate (immunotoxin)

2.1 mg of modified antibodies are incubated for 17 h at 25° C. with 2 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect The study is performed according to D(1) of Example 2 of the present patent application.

The values of the molar concentrations corresponding to a 50% inhibition of incorporation of the tracer ($IC_{50}$) are indicated in Table II. These values show that the potentiating effect of the ammonium ion is 150. This factor is much higher than that observed for ricin or the isolated A chain. Moreover, the ammonium ion has the remarkable property of increasing the selectivity of the immunotoxin. In fact, if the ratio of the $IC_{50}$ values of the A chain and the immunotoxin is taken as the criterion for selectivity of action of the immunotoxin, this ratio is 730 in the absence of activator and 19,000 in the presence of $NH_4Cl$.

EXAMPLE 9:

Conjugate obtained by reacting an anti-human T cell antibody fragment (antibody fragment directed against an antigen of MW=65 KD), substituted by an activated disulfide group, with the A chain of ricin

A - Anti-human T cell antibody fragment (or Fab T101)

The antibody fragment T101, or Fab T101, was obtained from the antibody T101 described in French Patent Application 81 21 836.

100 mg of antibody T101 are hydrolyzed with 1 mg of papain for 3 h at 37° C. in the presence of cysteine 10 mM and EDTA 1 mM. The reaction is stopped with iodoacetamide 20 mM for 1 h at 37° C. and the reaction medium is dialyzed against a phosphate buffer (10 mM, pH 7.0). The reaction medium is chromatographed on DEAE trisacryl and the antibody fragments T101 are recovered in the filtrate.

B - Activated anti-human T cell antibody 15.3 mg of Fab T101 are modified with 1.740 mg of SPDP in a total volume of 3.06 ml of phosphate buffer (0.125 M, pH 7.0) for 30 min at room temperature. The antibody fragments modified in this way are purified by dialysis against the same phosphate buffer (125 mM, pH 7.0) to remove the excess reagents.

C - Conjugate (immunotoxin)

12.7 mg of modified antibody fragments T101 are incubated for 17 h at 25° C. with 17 mg of A chain of ricin. The reaction medium is then purified by chromatography on ACA 44. The immunotoxin is obtained in the first chromatography peak.

D - Biological properties (1) Inhibition of protein synthesis in cells and potentiation of this effect The study is performed according to D(1) of Example 2 of the present patent application.

The values of the molar concentrations corresponding to a 50% inhibition of incorporation of the tracer ($IC_{50}$) are recorded in Table II. These values show that the potentiating effect of the ammonium ion is 134. This factor is much higher than that observed for ricin or the isolated A chain. Moreover, the ammonium ion has the remarkable property of increasing the selectivity of the immunotoxin. In fact, if the ratio of the $IC_{50}$ values of the A chain and the immunotoxin is taken as the criterion for selectivity of action of the immunotoxin, this ratio is 628 in the absence of activator and 14,600 in the presence of NH4Cl.

EXAMPLE 10:

Conjugate obtained by reacting an anti-human T cell antibody fragment (antibody directed against an antigen of MW=65 KD), substituted by an activated disulfide group, with the A chain of ricin A - Anti-human T cell antibody fragments (or F(ab')2T101)

The antibody fragments T101, or F(ab')2 T101, were obtained from the antibody T101 described in French Patent Application 81 21 836.

61.4 mg of antibody T101 are dialyzed against a sodium formate buffer (100 mM, pH 3.5) and then hydrolyzed with pepsin (5% by weight of antibody) for 1 h 30 min at 37° C. The reaction is stopped by bringing the pH of the solution to 7.0 with Tris buffer 1 M. The reaction medium is purified by filtration on a column of Sephadex G100. 12.5 mg of F(ab')2 are collected in the filtrate.

B - Activated anti-human T cell antibody fragment 5 mg of F(ab')2 T101 are modified with 0.135 mg of SPDP for 30 min at 25° C. The IgGs modified in this way are purified by dialysis against the same phosphate buffer (125 mM, pH 7.0) to remove the excess reagents.

C - Conjugate (immunotoxin)

3.96 mg of modified antibody fragments T101 are incubated for 18 h at 30° C. with 3.24 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect The study is performed according to D(1) of Example 2 of the present patent application.

The values of the molar concentrations corresponding to a 50% inhibition of incorporation of the tracer ($IC_{50}$) are recorded in Table II. These values show that the potentiating effect of the ammonium ion is 83. Moreover, the ammonium ion has the remarkable property of increasing the selectivity of the immunotoxin. In fact, if the ratio of the $IC_{50}$ values of the A chain and the immunotoxin is taken as the criterion for selectivity of action of the immunotoxin, this ratio is 4,400 in the absence of activator and 63,000 in the presence of NH4Cl.

EXAMPLE 11:

Conjugate obtained by reacting an anti-human T cell antibody (antibody directed against an antigen of MW=50 KD), substituted by an activated disulfide group, with the A chain of ricin A - Anti-human T cell antibody (or antibody RFT11)

This antibody, which is directed against CD2 (ref. 1), is an IgG1. It was obtained by the method described in ref.3. It undergoes a final purification by dialysis against phosphate buffer (125 mM, pH 7.0).

B - Activated anti-human T cell antibody 19 mg of antibody RFT11 are modified with 1.23 mg of pyridyldithiopropionic acid, activated beforehand by reaction with 0.73 mg of ethyldimethylaminopropylcarbodiimide, in a total volume of 3 ml of phosphate buffer (125 mM, pH 7.0) for 15 min at room temperature. The IgGs modified in this way are purified by dialysis against the same phosphate buffer (125 mM, pH 7.0) to remove the excess reagents.

C - Conjugate (immunotoxin)

15.9 mg of modified antibodies are incubated for 5 h at 25° C. with 6.4 mg of A chain of ricin. The reaction medium is then purified by chromatography on Sephadex G100. The immunotoxin is obtained in the first chromatography peak.

Moreover, a study performed by cytofluorometry made it possible to show that the anti-human T cell antibody used, the corresponding activated antibody and the conjugate of this antibody with the A chain of ricin had superimposable fluorescence histograms, allowing the assertion that the antibody had not undergone any significant degradation during the activation and coupling reactions to which it had been subjected and, in particular, that it was still capable, even within the conjugate, of recognizing the human T antigen against which it was directed.

The conjugate according to the invention, obtained above, was studied for its biological properties and, more especially, its anticancer action.

D - Biological properties (1) Inhibition of protein synthesis in cells and potentiation of this effect The cytotoxicity is evaluated by measuring the incorporation of $^{14}C$-leucine by the cells after incubation for 18 h at 37° C. in the presence of known quantities of the immunotoxin studied, or reference cytotoxic substances, in the presence or absence of ammonium chloride as a potentiator.

The results of the experiments performed are presented in the form of dose/effect curves, plotting, on the ordinate, the cytotoxic effect evaluated as indicated above and calculated in % of the value obtained on control cells in the absence of any cytotoxic substance, and, on the abscissa, the concentrations of the cytotoxic substances studied, expressed as molar concentrations of the toxic subunits of these substances.

Ammonium chloride was tested at a concentration of 10 mM. A previous check had been carried out to ensure that NH4Cl is not spontaneously cytotoxic to the cells employed at the concentrations indicated.

Figure 5:
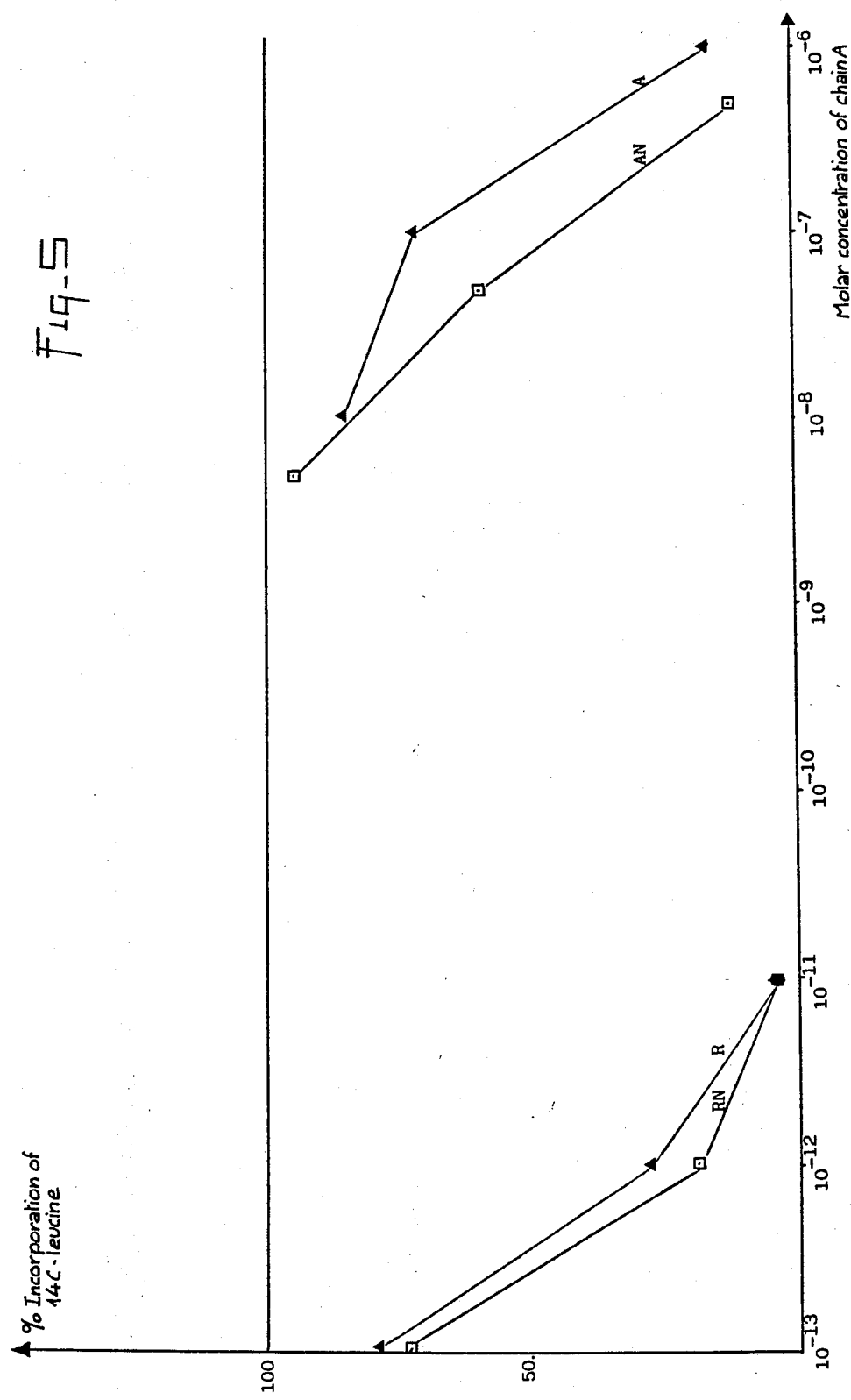
FIG. 5 shows cytotoxic activity on human T lymphoblastoid cells of the P12/ICHIKAWA line obtained with ricin and the A chain of ricin in the presence and absence of ammonium chloride.

FIG. 5 shows the respective results obtained on human T lymphoblastoid cells of the P12/ICHIKAWA line, carrying the target antigen.

The experimental conditions used and the symbols employed to characterize the curves obtained are indicated in the table below:

| A chain of ricin | A |
| ricin | R |
| A chain + NH4Cl 10 mM | AN |
| ricin + NH4Cl 10 mM | RN |

FIG. 5 shows the effects of ammonium chloride on the inherent cytotoxicity of ricin and isolated A chain, taken as reference substances. The values of the molar concentrations corresponding to a 50% inhibition of incorporation of the tracer ($IC_{50}$) are indicated in Table III.

TABLE III

| | on P12/ICHIKAWA cells | |
|---|---|---|
| Substances tested | With NH4Cl 10 mM | Without activator |
| Ricin | $3 \cdot 10^{-13}$ | $3.7 \cdot 10^{-13}$ |

TABLE III-continued

| | on P12/ICHIKAWA cells | |
|---|---|---|
| Substances tested | With NH₄Cl 10 mM | Without activator |
| A chain | $7.5 \cdot 10^{-8}$ | $2.5 \cdot 10^{-7}$ |

Figure 6:
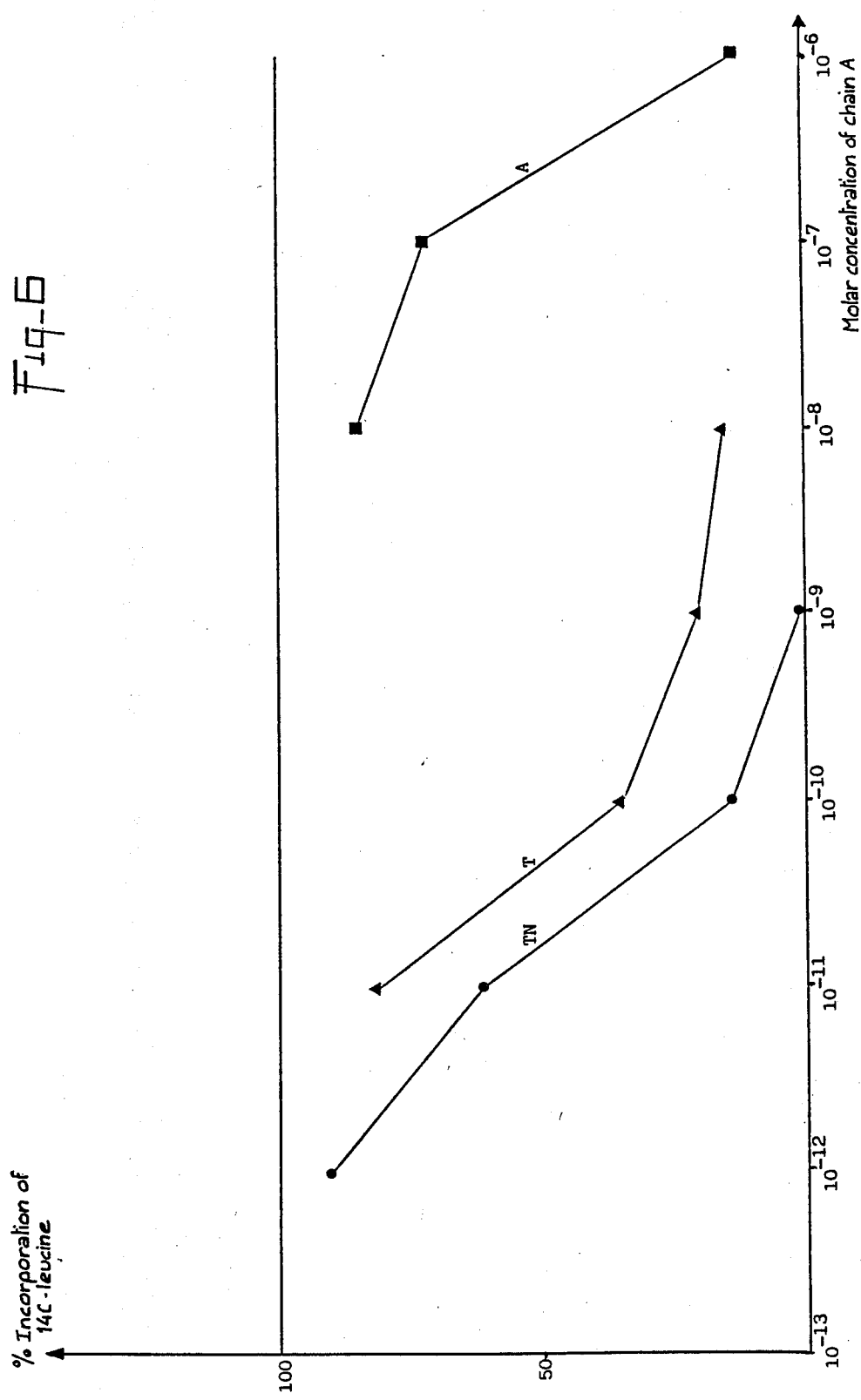
FIG. 6 shows cytotoxic activity on cells of the P12/ICHIKAWA line obtained with the A chain of ricin, the immunotoxin anti-T and the immunotoxin anti-T potentiated with ammonium chloride.

FIG. 6 shows the respective results obtained on P12/ICHIKAWA cells for:

| A chain of ricin | A |
|---|---|
| immunotoxin anti-T | T |
| immunotoxin anti-T + NH₄Cl 10 mM | TN |

The figure shows the potentiating effect of the ion $NH_4^+$ (10 mM) on the cytotoxicity of the immunotoxin anti-T towards cells of the P12/ICHIKAWA line.

The values of the molar concentrations corresponding to a 50% inhibition of incorporation of the tracer ($IC_{50}$) are recorded in Table IV.

TABLE IV on P12/ICHIKAWA cells
Molar concentrations corresponding to 50% inhibition of incorporation of the tracer

| Example | Antibody | $IC_{50}$ of non-potentiated immunotoxin | $IC_{50}$ of immunotoxin potentiated by NH₄Cl 10 mM |
|---|---|---|---|
| 11 | RFT11 | $4.5 \cdot 10^{-11}$ | $1.7 \cdot 10^{-11}$ |
| 12 | IIB5 | $2.2 \cdot 10^{-10}$ | $5.5 \cdot 10^{-11}$ |
| 13 | RL1T11 | $2.1 \cdot 10^{-10}$ | $1.5 \cdot 10^{-11}$ |

(2) Acceleration of the cytotoxicity kinetics

The effect of potentiating substances is not restricted to increasing the cytotoxic activity of the immunotoxins; it also makes it possible very substantially to accelerate the kinetics of the immunotoxins, as demonstrated by the following experiment.

By way of example, this experiment measured, as previously, the incorporation of radioactive tracer into the cells incubated with the immunotoxin, in the absence or presence of NH₄Cl 10 mM as a potentiator.

This experiment was carried out on the cellular model consisting of the P12/ICHIKAWA human T lymphoblastoid line with the immunotoxin anti-T at a concentration of $10^{-8}$ M. The results are presented in FIG. 7. This figure shows the results obtained by plotting the percentage incorporation of $^{14}C$-leucine (% of the control values) on the ordinate and the time in hours on the abscissa.

It is seen that, in the absence of potentiation, the expression of the cytotoxicity is very slow, as shown in curve (a). The value T10, which is the time required to obtain a 90% reduction in the incorporation of the tracer, is greater than 100 h. On the other hand, in the presence of NH₄Cl 10 mM, a considerable acceleration of the kinetics of expression of the cytotoxicity is apparent—curve (b)—since the value T10 is only 14 h 30 min here.

(3) Inhibition of the proliferation of stimulated human T lymphocytes

The studies are performed according to D(3) of Example 2 of the present patent and the results are shown in FIG. 8.

EXAMPLE 12:

Conjugate obtained by reacting an anti-human T cell antibody (antibody directed against an antigen of MW=50 KD), substituted by an activated disulfide group, with the A chain of ricin A - Anti-human T cell antibody (or antibody IIB5)

This antibody, which is directed against CD2 (ref. 1) is an IgG2a. It was obtained by the method described by S. Carrel, Lausanne, Switzerland. It undergoes a final purification by dialysis against phosphate buffer (125 mM, pH 7.0).

B - Activated anti-human T cell antibody 8 mg of antibody IIB5 are modified with 0.64 mg of pyridyldithiopropionic acid, activated beforehand by reaction with 0.38 mg of ethyldimethylaminopropylcarbodiimide, in a total volume of 4 ml of phosphate buffer (125 mM, pH 7.0) for 15 min at room temperature. The IgGs modified in this way are purified by dialysis against the same phosphate buffer (125 mM, pH 7.0) to remove the excess reagents.

C - Conjugate (immunotoxin)

8 mg of modified antibodies are incubated for 24 h at 25° C. with 3.4 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect This study is performed in a manner identical to D(1) of Example 11 of the present patent application.

The values of the molar concentrations corresponding to a 50% inhibition of incorporation of the tracer ($IC_{50}$) are indicated in Table IV.

The ammonium ion has the remarkable property of increasing the selectivity of the immunotoxin. In fact, if the ratio of the $IC_{50}$ values of the A chain and the immunotoxin is taken as the criterion for selectivity of action of the immunotoxin, this ratio is 1,000 in the absence of activator and 6,900 in the presence of NH₄Cl.

(2) Inhibition of the proliferation of stimulated human T lymphocytes

The studies are performed according to D(3) of Example 2 of the present patent and the results are shown in FIG. 8 (curve IT IIB5).

EXAMPLE 13:

Conjugate obtained by reacting an anti-human T cell antibody (antibody directed against an antigen of MW=50 KD), substituted by an activated disulfide group, with the A chain of ricin A - Anti-human T cell antibody (or antibody RL1T11)

This antibody, which is directed against CD2, is an IgG2a. It was obtained by J. C. Laurent (Centre de Recherche Clin-Midy/Sanofi - Montpellier - France) in the following manner: 4 weeks after the immunization of Balb/c mice with $10^7$ cells of the P12/ICHIKAWA human T lymphoblastoid line by intraperitoneal administration, a booster is administered intravenously with the same number of immunizing cells. Three days after the booster, the spleen cells of the immunized mice are fused with myeloma cells of the X63 Ag 8.653 murine line in the presence of PEG 40%. The clone 3A11 was selected because of its specificity for human T cells. This purified antibody undergoes a final dialysis against phosphate buffer (125 mM, pH 7.0).

B - Activated anti-human T cell antibody 3.25 mg of antibody RL1T11 are modified with 0.04 mg of SPDP for 30 min at room temperature in a total volume of 1.5 ml of buffer, pH 9.0. The IgGs modified in this way are purified by dialysis against the same buffer, pH 9.0, to remove the excess reagents.

C - Conjugate (immunotoxin)

1.87 mg of modified antibodies are incubated for 17 h at 25° C. with 0.94 mg of A chain of ricin. The reaction medium is then purified by chromatography on Sephadex G100. The immunotoxin is obtained in the first chromatography peak.

D - Biological properties (1) Inhibition of protein synthesis in cells and potentiation of this effect The study is performed according to D(1) of Example 11 of the present patent application.

The values of the molar concentrations corresponding to a 50% inhibition of incorporation of the tracer ($IC_{50}$) are recorded in Table IV.

The ammonium ion increases the selectivity of the immunotoxin. In fact, if the ratio of the $IC_{50}$ values of the isolated A chain and the immunotoxin is taken as the criterion for selectivity of action of the immunotoxin, this ratio is 1,000 in the absence of activator and 2,500 in the presence of $NH_4Cl$.

EXAMPLE 14:

Association of several immunotoxins for the allografting of bone marrow and/or immunosuppression in vivo for the treatment of certain autoimmune diseases and/or the treatment in vivo of malignant T proliferations and/or for the autographing of bone marrow in the case of patients suffering from malignant T proliferation (1) Anti-human T cell antibodies and immunotoxins Immunotoxin anti-CD5 or IT anti-T65 or IT T101 described in French Patent Application No. 81 21 836

Immunotoxin anti-CD7 or IT 3A1 described in Example 2

Immunotoxin anti-CD7 or IT A1 described in Example 3

Immunotoxin anti-CD2 or IT RFT11 described in Example 11

Immunotoxin anti-CD2 or IT IIB5 described in Example 12

Immunotoxin anti-CD7 or IT 8A6 described in Example 6

(2) Cytotoxic properties of the association of several immunotoxins for the depletion of stimulated human T cells The association of several immunotoxins directed against different T cell antigens must make it possible, according to these associations, to destroy all or part of the T lymphoid population.

In physiological and pathological situations, as in numerous experimental models, the T lymphocytes isolated from peripheral blood or from bone marrow have the property of responding to a variety of stimulations by proliferating. It is this proliferative response which we studied.

By way of example, lymphocytes from human peripheral blood, purified by Ficoll gradient centrifugation, are incubated in the presence of known concentrations of immunotoxin or reference cytotoxic substance and a final concentration of 10 mM of ammonium chloride for 24 h at 37° C. The cells are then washed and brought into contact with a mitogenic agent specific for human T cells, which consists of a mixture of phytohemagglutinin A (PHA) (Wellcome Ltd., 1% final concentration) and "T cell growth factor" (or TCGF or interleukine 2 or IL2) at a final concentration of 0.5 unit/ml. The residual cells capable of proliferating are analyzed 72, 96 and 120 h after the cytotoxic treatment has ended by means of indirect immunofluorescence using a flux cytofluorometer (FACS IV Becton Dickinson).

FIG. 8 shows the respective results obtained on human T lymphocytes from peripheral blood, stimulated with:

A chain of ricin $10^{-8}$ M + $NH_4Cl$ $10^{-2}$ M : A immunotoxin 3A1 $10^{-8}$ M + $NH_4Cl$ $10^{-2}$ M : IT 3A1 immunotoxin A1 $10^{-8}$ M + $NH_4Cl$ $10^{-2}$ M : IT A1 immunotoxin T101 $10^{-8}$ M + $NH_4Cl$ $10^{-2}$ M : IT T101 immunotoxin RTF11 $10^{-8}$ M + $NH_4Cl$ $10^{-2}$ M: IT RFT11 immunotoxin IIB5 $10^{-8}$ M + $NH_4Cl$ $10^{-2}$ M : IT IIB5 immunotoxin 8A6 $10^{-8}$ M + $NH_4Cl$ $10^{-2}$ M : IT 8A6

The association IT 3A1 + IT T101 $10^{-8}$ M + $NH_4Cl$ $10^{-2}$ M = curve 1.

The association IT 3A1 + IT T101 + IT RFT11 $10^{-8}$ M + $NH_4Cl$ $10^{-2}$ M = curve 2.

The association IT 3A1 + IT T101 + IT IIB5 $10^{-8}$ M + $NH_4Cl$ $10^{-2}$ M = curve 3.

The association IT A1 + IT T101 + IT RFT11 $10^{-8}$ M + $NH_4Cl$ $10^{-2}$ M = curve 4.

The association IT T101 + IT RFT11 $10^{-8}$ M + $NH_4Cl$ $10^{-2}$ M = curve 5.

The association IT T101 + IT IIB5 $10^{-8}$ M + $NH_4Cl$ $10^{-2}$ M = curve 6.

The association IT T101 + IT 8A6 $10^{-8}$ M + $NH_4Cl$ $10^{-2}$ M = curve 7.

What is claimed is:

1. In a process for preparing a composition comprising a conjugate of the chain A of ricin coupled by means of a disulfide bridge with an antibody directed against human T cells, the improvement comprises adding to said conjugate an amount of ammonium chloride effective to increase the cytotoxic activity of said conjugate.

* * * * *